United States Patent [19]

Klemann et al.

[11] 4,216,191

[45] Aug. 5, 1980

[54] METHOD OF PREPARING INORGANIC-ALKALI METAL SALTS

[75] Inventors: Lawrence P. Klemann, Somerville; Eugene L. Stogryn, Edison, both of N.J.

[73] Assignee: Exxon Research & Engineering Co., Florham Park, N.J.

[21] Appl. No.: 35,055

[22] Filed: May 1, 1979

[51] Int. Cl.$^2$ .............................................. C01C 3/20
[52] U.S. Cl. ................................... 423/364; 423/365; 423/366; 423/385; 423/395; 423/415 R; 423/476; 423/499; 423/593
[58] Field of Search ............... 423/499, 364, 365, 366, 423/385, 395, 476, 593, 415

[56] References Cited

U.S. PATENT DOCUMENTS

| | | | |
|---|---|---|---|
| 3,047,363 | 7/1962 | Field et al. | 423/366 |
| 3,049,406 | 8/1962 | Grant et al. | 423/499 |

FOREIGN PATENT DOCUMENTS 243727 3/1963 Australia ................................. 423/366

Primary Examiner—Wayne A. Langel
Attorney, Agent, or Firm—Kenneth P. Glynn

[57] ABSTRACT

The present invention is directed to a method of preparing an inorganic-alkali metal salt of the formula:

$$ZY$$

wherein Z is an alkali metal selected from the group consisting of lithium and sodium, and wherein Y is an inorganic radical selected from the group consisting of SCN, CN, CNS, OCN, Br, I, Cl, $NO_2$, $NO_3$, $ClO_4$, $ReO_4$, and $CF_3SO_3$. The method involves the reaction of a nitrogen-containing compound of the formula:

$$QHY$$

wherein Q is selected from the group consisting of specified nitrogen-containing groups, and wherein H is hydrogen and Y is as defined above, with an alkali metal compound of the formula:

$$ZX$$

wherein Z is defined above and wherein X is selected from the group consisting of hydrogen, specified nitrogen-containing radicals, and specified organic radicals. The reaction is carried out in ether solvent. In a preferred embodiment, Q is $NH_3$ and X is hydrogen.

8 Claims, No Drawings

METHOD OF PREPARING INORGANIC-ALKALI METAL SALTS

BACKGROUND OF THE INVENTION AND PRIOR ART

1. Field of the Invention

The present invention relates to a method of preparing high purity, anhydrous alkali metal salts of the inorganic-alkali metal type. More particularly, the present invention is directed to the method of preparing such compounds by reacting specified nitrogen-containing compounds with specified alkali metal-containing compounds, as more fully developed below.

2. Description of the Prior Art

There have been many techniques developed over the past few years for the synthesis of inorganic—as well as organic—alkali metal salts. For example, Kunze et al, J. Phys. Chem. 67, 385 (1963) describe the preparation of lithium tetraphenyl boride by the reaction of sodium tetraphenyl boride with lithium chloride in ethanol, and Bhattacharyya et al, J. Phys. Chem. 69, 608 (1965) describe the preparation of alkali metal tetraphenyl boride salts by the reaction of sodium tetraphenyl boride with lithium chloride in THF solvent. Revzin et al, Chemical Abstracts 70, 28974 q (1969) and Chemical Abstracts 71, 3416 s (1969) describe the preparation of lithium tetraphenyl boride from various salts, including ammonium tetraphenyl boride with lithium-containing ion exchange resins in acetone. Likewise, Kirgintsev et al, Chemical Abstracts 72, 139078 m (1970) describe the formation of lithium tetraphenyl borate and sodium tetraphenyl borate using potassium tetraphenyl borate with an ion exchange resin of the lithium form and using acetone solvent. Kozitskii, Chemical Abstracts 79, 83825 c (1973) describe the preparation of lithium tetraphenyl borate and the like by reaction of the potassium analogue with a lithium-containing ion exchange resin in the presence of acetone and water. (It should be noted that various prior art references refer to the same compounds as tetraphenyl borate or as tetraphenyl borides). Khol'kin et al, Chemical Abstracts 85, 86471 u (1976) describe the preparation of lithium tetraphenyl boride from sodium tetraphenyl boride but do not describe the source of lithium except to point out that it is an exchange synthesis, i.e., exchange extraction synthesis. Witting et al, Ann. 563, 110 (1949) and Chemical Abstracts 46, 6607 d (1952) respectively teach the preparation of lithium tetraphenyl boride and the like from triphenyl boron and trifluoro boron sources reacted with lithium phenyl salt in ether solvents. Grassberger et al, Angew. Chem. Int. Ed. Engl. 8, 275 (1969) describe the preparation of various alkali metal tetraorganyl borates by reaction of, for example, triphenyl boron with lithium tetraethyl boride without solvent.

Lee, Inorg. Chem., Volume 3, No. 2, February 1964, pp. 289–90 describes the synthesis of lithium thiocyanate from hydrated lithium hydroxide and ammonium thiocyanate. Olah et al, Journal of the American Chemical Society, 97, No. 12, pp. 3559–3561 (1975) describe the synthesis of $LiO_2CCF_3$ from lithium hydride and $NH_4O_2CCF_3$. Morosi et al, Chemical Physics Letters, Volume 47, No. 2, pp. 396–398 (1977) describe a theoretical analysis of a hypothetical reaction between the ammonium ion and lithium hydride in the gas phase to yield lithium salts. U.S. Pat. No. 3,049,406 describes the preparation of anhydrous lithium salts, including lithium halides, lithium pseudohalides, such as lithium cyanide and lithium thiocyanate, by the reaction of lithium hydride with halogens, cyanogen or thiocyanogen in an ether solution.

Notwithstanding all of the aforementioned prior art directed to various methods of preparing alkali metal salts, to date no reference has been published which teaches or renders obvious the methods of preparation described herein.

BRIEF DESCRIPTION OF THE INVENTION

The present invention is directed to a method of preparing an inorganic alkali metal salt of the formula:

$$ZY \qquad (1)$$

wherein Z is an alkali metal selected from the group consisting of lithium and sodium, and wherein Y is an inorganic radical selected from the group consisting of SCN, CN, CNS, OCN, Br, I, Cl, $NO_2$, $NO_3$, $ClO_4$, $ReO_4$, and $CF_3SO_3$.

The method involves the reaction of a nitrogen-containing compound of the formula:

$$QHY \qquad (2)$$

wherein Q is selected from the group consisting of specified nitrogen-containing groups, wherein H is hydrogen and wherein Y is as defined above, with an alkali metal compound of the formula:

$$ZX \qquad (3)$$

wherein Z is defined above and wherein X is selected from the group consisting of hydrogen, specified nitrogen-containing radicals, and specified organic radicals. The reaction is carried out in ether solvent.

DETAILED DESCRIPTION OF THE INVENTION

The present invention is directed to a method of preparing an organic-alkali metal salt of the Formula (1) described above, namely:

$$ZY$$

wherein Z is an alkali metal selected from the group consisting of lithium and sodium, and wherein Y is an inorganic radical selected from the group consisting of SCN, CN, CNS, OCN, Br, I, Cl, $NO_2$, $NO_3$, $ClO_4$, $ReO_4$, and $CF_3SO_3$. Of these, Y is desirably Br, I, $CF_3SO_3$ and SCN, with SCN being preferred.

Included among the alkali metal salts which may be prepared by the present invention are:
LiSCN
NaSCN
NaCN
NaCNS
NaOCN
LiBr
LiI
LiCl
$NaNO_2$
$LiNO_3$
$LiClO_4$
$LiReO_4$ and
$LiCF_3SO_3$ The method of the present invention involves reacting nitrogen-containing compound of the formula:

$$QHY \qquad (2)$$

wherein Q is selected from the group consisting of $NH_3$; $N(CH_3)_3$; $HN(CH_3)_2$; $H_2NCH_3$; $N(C_2H_5)_3$; $HN(C_2H_5)_2$ and $H_2NC_2H_5$, wherein H is hydrogen and wherein Y is as defined above, in ether solvent with an alkali metal compound of the formula:

$$ZX \qquad (3)$$

wherein Z is as defined above and wherein X is selected from the group consisting of H; $NH_2$; $N(CH_3)_2$; $HNCH_3$; $N(C_2H_5)_2$; $HNC_2H_5$; $N(i-CH(CH_3)_2)_2$;—$CH_3$; —$C_2H_5$; and —$C_6H_5$.

Desirably, the variable Q in Formula (2) is selected from the group consisting of $NH_3$ and the mentioned tertiary amines, and is preferably $NH_3$. Desirably, the variable Y in Formula (2) is selected from the group consisting of Br, I, $CF_3SO_3$ and SCN, and is preferably SCN.

In the alkali metal compound of Formula (3) above, the variable Z is lithium or sodium and is preferably lithium. Also, the variable X is desirably hydrogen, $NH_2$; $N(CH_3)_2$ and $HNCH_3$.

The reaction of the present invention is performed in ether solvent, as mentioned. Among the ethers which may be employed are dioxolane, dimethoxyethane, diglyme, tetrahydrofuran, methyltetrahydrofuran, tetrahydropyran, dioxane and diethyl ether, as well as mixtures thereof. Desirably, the ether solvent may be diethyl ether, dioxolane, dimethoxyethane, 2-methyltetrahydrofuran and mixtures thereof. Preferably, the ether solvent may be selected from diethyl ether, dioxolane and 2-methyltetrahydrofuran.

In performing the synthesis of the present invention, the nitrogen-containing compound of Formula (2) is reacted with the alkali metal compound of Formula (3) in ratios so as to achieve a desirable amount of reaction product. Although it is not essential to the process, it is particularly advantageous to combine these two reactants so as to have a stoichiometric excess of the alkali metal compound of Formula (3). Concerning the ether solvent, it is desirable but not essential that adequate solvent be used so as to dissolve all of the desired reactant materials. In general, at least about 0.5 to about 50 milliliters of solvent per 1.0 gram of total reactants is useful. Preferably, at least about 2.0 to about 20 milliliters of solvent per 1.0 gram of total reactants may be used.

These reactions may be carried out at any operable pressure and temperature, and room temperature and pressure conditions will allow these reactions to readily occur in most instances. It may also be advantageous to pass an inert gas such as $N_2$, He, or Ar through or over the condensed reaction mixture so as to purge by-products including $H_2$ and volatile amines. Also, in some instances, it is preferable to employ elevated temperatures, especially at reflux temperatures of the solvent-reactant systems. For example, reaction temperatures in the range of about 0° C. to about 175° C. may be used.

By the process of the present invention, significant advantages are achieved over prior art synthesis techniques. For example, by using the method of the present invention, anhydrous lithium salts may be obtained without requiring additional finishing steps to remove water. Also, the inorganic-alkali metal salts produced may be used in situ in their solvent solution, or they may be isolated in solid form by conventional separation techniques. Further, using the ZX type reactant, the need to carefully control the stoichiometric ratio of the reactants is eliminated. Due to the very limited solubility of some of these ZX type reactants, excess may be used and only that which is stoichiometrically required by the reaction dissolves and is consummed. The presence of excess ZX serves as a gettering agent capable of removing from the solvent traces of water which are often considered undesirable for alkali metal salt solutions. This added benefit insures an anhydrous solution which may be useful directly in high purity applications, e.g., as electrolytes in alkali metal anode batteries.

The present invention is illustrated in detail by the following examples. However, these examples are presented for illustrative purposes only and the invention should not be construed to be limited thereto.

EXAMPLE 1

Lithium hydride (4.70 g, 0.587 mole) and dioxolane (150 mL) are charged to a 250 mL flask, fitted with a magnetic stirrer, condenser, nitrogen inlet, and solids addition arm. through the latter anhydrous $NH_4SCN$ (19.0g, 0.25 mole) is added. A vigorous reaction results and ammonia is detected in the effluent gas stream. After stirring at reflux about 24 hours, the mixture is cooled and filtered. Unreacted LiH (2.6 g, 0.327 mole) is recovered indicating that 0.26 mole reacts with the $NH_4SCN$. Concentration of the clear filtrate yields 32 g of white solid which contains dioxolane as shown by NMR analysis in dimethoxyethane.

Analysis

Calc. for LiSCN Dioxolane, MW 139.060: C 34.52; H 4.35; N 10.07; Li 4.99. Found: C 31.91, 31.33, 31.10; H 4.30, 4.48, 4.52; N 10.50, 9.59, 9.77; Li 5.10.

Agreement between experiment and theory is very good for H, N, and Li in support of the solvate composition. Experience shows that low values for C are expected due to prevolatalization of complexed dioxolane and concommitant incomplete combustion.

EXAMPLE 2

$NH_4SCN$ (39 g, 0.5 mole) and 500 mL of diethyl ether (dried over $CaH_2$) were combined in a 1000 mL flask fitted with a reflux condenser, a magnetic stirrer bar, a nitrogen line, and a side arm attached by a short length of Gooch tubing to a 125 mL Erlenmeyer flask containing LiH (8.0 g, 1 mole). The LiH was added in portions over one hour and the reaction produced was sufficiently exothermic so as to bring the mixture to reflux. After heating the mixture at reflux for an additional 24 hours, the mixture was cooled and excess LiH was removed by filtration. Stripping the filtrate afforded about 45 g of crude, ether containing, product. This was evacuated at $10^{-3}$ Torr for one day at room temperature then two days at 95°–98° C. The final yield was 32.2 g (quantitative) of LiSCN which was free of ether as determined by an nmr analysis of a DME solution.

What is claimed is:

1. A method of preparing an alkali metal salt of the formula:

$$ZY$$

wherein Z is an alkali metal selected from the group consisting of Li and Na, and wherein Y is an inorganic radical selected from the group consisting of SCN, CN, CNS, OCN, Br, I, Cl, $NO_2$, $NO_3$, $ClO_4$, $ReO_4$, and $CF_3SO_3$ comprising:

reacting in ether solvent, a nitrogen-containing compound of the formula:

QHY wherein Q is selected from the group consisting of $NH_3$; $N(CH_3)_3$, $HN(CH_3)_2$; $H_2NCH_3$; $N(C_2H_5)_3$; $HN(C_2H_5)_2$ and $H_2NC_2H_5$, wherein H is hydrogen and wherein Y is as defined above, with an alkali metal compound of the formula:

ZX wherein Z is as defined above and wherein X is selected from the group consisting of H; $NH_2$; $N(CH_3)_2$; $HNCH_3$; $N(C_2H_5)_2$; $HNC_2H_5$; $N(i-CH(CH_3)_2)_2$; $-CH_3$; $-C_2H_5$; and $-C_6H_5$.

2. The method of claim 1 wherein said variable Y is selected from the group consisting of Br, I, $CF_3SO_3$ and SCN.

3. The method of claim 2 wherein X is selected from the group consisting of H; $NH_2$; $N(CH_3)_2$ and $HNCH_3$.

4. The method of claim 2 wherein X is selected from the group consisting of H and $NH_2$.

5. The method of claim 2 wherein said solvent is selected from the group consisting of diethyl ether, dioxolane, dimethoxyethane, and 2-methyltetrahydrofuran.

6. The method of claim 2 wherein a stoichiometric excess of the alkali metal compound ZX is used.

7. The method of claim 1 wherein said ether solvent is selected from the group consisting of dioxolane, dimethoxyethane, diglyme, tetrahydrofuran, 2-methyltetrahydrofuran, tetrahydropyran, dioxane and diethyl ether.

8. The method of claim 1, 2, 3, 4, 5, 6 or 7 wherein the alkali metal Z is lithium.

* * * * *